United States Patent [19]
Hedner et al.

[11] Patent Number: 6,083,756
[45] Date of Patent: Jul. 4, 2000

[54] PREVENTION OF SUDDEN INFANT DEATH

[75] Inventors: Jan Hedner, Gothenburg; Anders Pettersson, Kode, both of Sweden

[73] Assignee: Diabact AB, Sweden

[21] Appl. No.: 09/068,363

[22] PCT Filed: Nov. 6, 1996

[86] PCT No.: PCT/SE96/01428

§ 371 Date: May 7, 1998

§ 102(e) Date: May 7, 1998

[87] PCT Pub. No.: WO97/17612

PCT Pub. Date: May 15, 1997

[30] Foreign Application Priority Data

Nov. 7, 1995 [SE] Sweden ................................. 9503937

[51] Int. Cl.[7] .............................. G01N 33/48; A61B 5/08
[52] U.S. Cl. ........................... 436/63; 436/513; 436/900; 435/7.92; 600/300; 600/532; 600/543; 422/83; 422/84
[58] Field of Search ..................................... 600/300, 532, 600/543; 422/83, 84; 436/63, 513, 900; 435/7.92

[56] References Cited

U.S. PATENT DOCUMENTS 5,848,975  12/1998  Phillips .................................... 600/532

OTHER PUBLICATIONS

Blecker et al., Journal of Clinical Microbiology, vol. 31, No. 7, Jul. (1993), pp. 1770–1773.

Dialog Information Service, File 155, Medline, Dialog Accession No. 08367085, G. Oderda, et al., "Eighteen Month Follow Up of Helicobacter Pylori Positive Children Treated With Amoxycillin and Tinidazole", & Gut (England), Oct. 1992, vol. 33, No. 10, pp. 1328–1330.

Dialog Information Service, File 155, Medline, Dialog Accession No. 09124837, Medline Accession No. 95054837, U. Blecker, et al., "Evolution of Helicobacter Pylori Positivity in Infants Born From Positive Mothers", J. Pediatr. Gastroenterol. Nutr. (United States), Jul. 1994, vol. 19, No. 1, pp. 87–90.

Dialog Information Service, File 155, Medline, Dialog Accession No. 08918853, Medline Accession No. 94233853, T.G. Murrell, et al., "Sudden Infant Death Syndrome (SIDS): Are Common Bacterial Toxins Responsible, and Do They Have a Vaccine Potential?", Vaccine (England), Mar. 1994, vol. 12, No. 4, pp. 365–368.

Dialog Information Service, File 155, Medline, Dialog Accessiion No. 09172550, Medline Accession No. 95102550, C.C. Blackwell, et al., "The Role of Infectious Agents in Sudden Infant Death Syndrome", FEMS Immunol. Med. Microbiol (Netherlands), Aug. 1994, vol. 9, No. 2, pp. 91–100.

*Primary Examiner*—Dwayne C. Jones
*Assistant Examiner*—C. Delacroix-Muirheid
*Attorney, Agent, or Firm*—Ostrolenk, Faber, Gerb & Soffen, LLP

[57] ABSTRACT

A method for identification of an infant being particularly susceptible to sudden infant death syndrome (SIDS) comprises the determination of an *Helicobacter pylori* infection in the infant's mother, particularly by detection of antibodies to *H. pylori* of the IgG type, in a blood sample drawn from the infant's mother or by determination of carbon dioxide formed from urea in the air exhaled from the infant's mother upon oral administration of a challenge dose of urea. Also disclosed is the use of an antibiotic effective against *H. pylori* for the manufacture of a medicament for administration to mothers and other persons infected by *H. pylori* and coming into close bodily contact with infants below two years of age, and a method of prevention of SIDS by administration of that antibiotic.

5 Claims, No Drawings

PREVENTION OF SUDDEN INFANT DEATH

This application is a 371 of PCT/SE96/01428, filed Nov. 6, 1996.

FIELD OF THE INVENTION

The present invention relates to the identification of infants with increased risk of sudden death (sudden death syndrome; SIDS), and to methods and means for SIDS prevention.

BACKGROUND OF THE INVENTION

Sudden infant death syndrome (SIDS) occurs in young infants during a narrow time range that peaks at 3 months and extends over about two years from birth. It is relatively common (7,000 deaths in the United States per year). Usually it is defined in the negative: "The sudden death of any infant or young child which is unexpected in history and in which a thorough post-mortem examination fails to demonstrate an adequate cause for death".

SIDS is believed to have multiple causal mechanisms for which various theories have been forwarded. One potential cause of SIDS is the sudden cessation of ventilation (apnea; for a survey, see Thach B T, Apnea and the Sudden Infant Death Syndrome, Saunders N & Sullivan C, Eds., Lung Biology in: *Health and Disease,* Vol. 7/I, Marcel Dekker, New York 1994, p. 649–671. In most cases, life-threatening episodes of apnea in infants can be managed by stimulation or by artificial respiration provided apnea is detected at once and appropriate measures are taken immediately upon detection. Close surveillance of infants at risk thus is indicated.

Several factors identified in epidemiological studies of SIDS are associated with increased susceptibility of infants to infectious diseases, particularly upper respiratory tract infections. The period in which infants are at highest risk roughly corresponds to the period when maternal antibodies in the infant are decreasing while its immature immune system is not able to provide full compensation. The vast majority of SIDS-related deaths occur below the age of two years. Not only are breast-fed infants less vulnerable to infections but also less susceptible to SIDS. Many babies who died from SIDS had mild gastrointestinal tract infection shortly before death; IgA response of their duodenal mucosa was found to be significantly increased (Stoltenberg L et al., *Pediatr. Res.* 32 (1992) 372–375).

In the apnea hypothesis for SIDS, the cause of death is thought to be suffocation. The infant suddenly stops breathing. This might be caused, for instance, by acute upper airway obstruction, gastroesophageal reflux or abnormal cardiopulmonary control.

Means for identifying SIDS-prone infants are lacking. Close monitoring of infants identified being at SIDS risk can be expected to substantially reduce mortality. Pharmaceutical means for preventing SIDS in infants are lacking. Their possible use would require identification of infants at risk.

OBJECTS OF THE INVENTION

It is an object of the invention to provide a means for identification of infants susceptible to SIDS.

It is another object of the invention to provide pharmaceutical means and methods for their use for the prevention of SIDS.

SUMMARY OF THE INVENTION

The present invention is based on the insight that the incidence of SIDS is substantially increased in infants whose mothers test positive for IgG antibodies to *Helicobacter pylori* (*H. pylori*) and that the mothers may transfer infection with *H. pylori* to their children. It is also based on the insight that, to a lesser extent, *H. pylori* transmission may be caused by other members of the family or persons in frequent and bodily close contact with the infant. Furthermore, the present invention is based on the insight that, as a preventive measure against SIDS in infants, mothers infected by *H. pylori* should be treated rather than their children; the same concept holds true for said other members of the family or persons in close contact with the infant. However, there is no reason for not treating infants once they have been infected with *H. pylori*. Once these insights have been gained, it is evident that preventive measures should be taken as early as possible, preferably ante partum. In this context, it should be noted that only a small proportion of infected persons, perhaps 15 to 20 percent, will have an ulcer during their lifetime. Thus the vast majority of persons infected with *H. pylori* will be unaware of their infection.

As already mentioned above, one possible cause of death in SIDS is suffocation. Such suffocation may be triggered, for instance, by gastroesophageal reflux to which infection by *H. pylori* may inducive.

According to the present invention is provided a method for identification of an infant being substantially susceptible to SIDS, comprising the determination of an *H. pylori* infection in the infant's mother or in a member of the infant's family or a person expected to come into close bodily contact with the infant. In consequence such risk is already existant for a fetus, and said determination of the infection should preferably be carried out ante partum to allow ante-partum treatment of a possible *H. pylori* infection in the mother or other person(s) expected to come into close bodily contact with the infant. This should minimize the risk for transmission of the infection to the infant. It is also preferred to test asymptomatic infants for infection by *H. pylori* to identify those being at SIDS risk.

According to one aspect of the invention, it is preferred for said method to comprise the determination of antibodies, particularly of antibodies of the IgG type, to *H. pylori* in a blood sample drawn from the infant's mother or from said close relative or other person. Testing is also preferred for corresponding IgA or IgM antibodies.

According to another aspect of the invention, it is preferred for said method to comprise the detection of carbon dioxide formed from urea in the air exhaled from the infant's mother or close relative or said other person upon oral administration of a challenge dose of urea. The urea challenge dose preferably comprises urea marked with $^{13}$C. Less preferred is $^{14}$C marked urea. Infection by *H. pylori* can also be demonstrated by identification of DNA specific for *H. pylori* in saliva, dental plaque, blood or faeces, for instance by PCR techniques.

According to the present invention is also disclosed the use of an antibiotic or a combination of antibiotics effective against *H. pylori* for the manufacture of a medicament for administration to mothers or prospective mothers infected by *H. pylori* lacking symptoms of gastric ulcer and having infants whose immune system is under development. Treatment *H. pylori* infections in mothers of infants is indicated independently of the presence of gastric ulcer. It is also preferred to administer said antibiotic to the infant or to both mother and infant. Also preferred is a corresponding use in respect of *H. pylori*-infected relatives of the infant or infected other persons expected to come into close bodily contact with the infant, said relatives or other persons having no symptoms of gastric ulcer. In this specification the term "gastric ulcer" also comprises duodenal ulcer; specific mention of duodenal ulcer is only made if there is a reason to distinguish between gastric and duodenal ulcer.

According to the present invention is provided a method for prevention of SIDS in infants, said method comprising the administration of a therapeutically effective amount of an antibiotic or a combination of antibiotics effective against *H. pylori* to a pregnant woman or the mother of an infant having an immature immune system, the pregnant women or mother lacking symptoms of gastric ulcer. Similarly is preferred such administration to close relatives and other persons expected to come into close bodily contact with the infant.

According to the present invention is furthermore provided a method for prevention of SIDS in infants whose immune system is under development, said method comprising the administration of a therapeutically effective amount of an antibiotic or a combination of antibiotics effective against *H. pylori* to the infant.

The present invention will be more fully explained by reference to the following preferred embodiments which, however, are given for purposes of illustration only and are not intended to limit the invention.

PREFERRED EMBODIMENTS OF THE INVENTION

EXAMPLE 1

Controlled Clinical Study of Mothers of Infants Who Died by SIDS

SIDS mothers (n=28) were caucasian women having lost a child in SIDS during the period from 1989 to 1994 and living in the area of Göteborg, Sweden. As controls was chosen a sample of 53 women from the same area and having had a child born during the same period. All women completed a questionaire about smoking habits, length of education, and occupation.

Blood was collected by venipuncture, and serum samples analyzed for the presence of *H. pylori* IgG by an in-house, standard ELISA method (specificity 98%, sensitivity 94%). Comparisons between the SIDS mothers and the controls were performed by Fisher's permuation test (Odén A et al., *Annals of Statistics* 3 (1975) 518–520) and by Mantel's test (Mantel N, *J. American Stat. Ass.* 58 (1963) 690–700) with the elimination of age. The age-adjusted odds ratio was estimated by a logistic regression model. Two-tailed tests were used.

Results are given in Table 1.

TABLE 1

IgG antibodies to *Helicobacter pylori* in SIDS mothers and controls

| Age | SIDS mothers | | Controls | |
| --- | --- | --- | --- | --- |
| | *H. pylori*-positive | *H. pylori*-negative | *H. pylori*-positive | *H. pylori*-negative |
| 20–24 | | | | 2 |
| 25–29 | | 5 | 1 | 15 |
| 30–34 | 4 | 2 | 1 | 15 |
| 35–40 | 5 | 2 | 3 | 15 |
| 40–44 | 5 | 3 | 1 | 12 |
| 44–49 | | 1 | 1 | |

The age of SIDS mothers (mean 36 years) was significantly higher than of the controls (mean 33 years), p<0.05. There was no significant difference in respect of smoking habits (p>0.30) and length of education (p>0.30). The prevalence of *H. pylori* among SIDS mothers was significantly higher than among controls (p=0.0073) when eliminating the influence of age. The age-adjusted odds ratio was 5.2 (95% confidence interval: 1.7–15.9). The prevalence of *H. pylori* seropositivity among control mothers was 13%, a figure which is consistent with that for the entire Swedish population.

In a population with a *Helicobacter pylori* seropositivity of 20%, the elimination of the infection in mothers would result in SIDS reduction by 46% at an odds ratio of 5.2.

EXAMPLE 2

Urea Breath Test

The Urea Breath Test (UBT) is based on the expression of urease by *H. pylori* in the acidic environment of the stomach. Urease catalyzes the hydrolysis of urea into ammonia and carbon dioxide which equilibrates with body carbon dioxide/carbonate. Urea marked with $^3C$ or $^{14}C$ and administered orally to a patient infected by *H. pylori* forms $^{13}CO_2$ or $^{14}CO_2$, respectively, upon entering the stomach. The isotope-marked carbon dioxide equilibrates and can be detected in the exhaled air. $^{14}C$ can be easily detected by scintillography but has the drawback of being radioactive. The detection of the stable isotope $^{13}C$ requires more expensive detection techniques, such as mass spectrometry, but recent developments in IR and laser spectrometry, for instance, should reduce the cost of $^{13}C$ analyses.

An important aspect of detection and measurement of *H. pylori* urease activity is interference of such activity present in the oral cavity and the lower gastrointestinal tract. This problem can be solved by encapsulating the marked urea in a capsule that will disintegrate in the stomach, and by proper timing of the measurement which is preferably carried out within 10 to 60 min from the time of oral administration.

The following test protocol is recommended:
1. exhaled air is analysed with the patient in a fasting condition,
2. a calorie-rich meal is given,
3. 10 min from the end of intake of the meal, the patient is made to drink a solution of 100 mg $^{13}C$-urea in 50 ml of water,
4. the patient is put in a lateral recumbent position and turned over to the other lateral position in intervals,
5. two liters of exhaled air are collected at intervals of 5 min starting 20 min post administration,
6. 20 ml samples of collected air are analyzed, for instance in a mass spectrometer after separation of carbon dioxide by absorption on a weakly basic material, such as a weakly basic ion exchange resin in free base form. Peaks at m=44 and m=45 represent $C^{12}$ and $^{13}C$ carbon dioxide. The increase in m=44/45 peak ratio is monitored for detection of carbon dioxide formed from $^{13}C$-marked urea by urease.

It should be observed that the method is not reliable in patients undergoing anti-ulcer therapy by means of certain medicines, such as medicines of the proton pump inhibitor type, increasing gastric pH above about 4.0.

Detailed descriptions of the $^{13}C$ breath test is described in the: Marshall B J et al., *Am. J. Gastroenterology* 86 (1991) 438–445; Graham D Y et al., *Lancet* 1987, 1174–1177; Logan R P H et al., *Eur. J. Gastroenterol. Hepatol.* 3 (1991) 915–021; these publications are incorporated herein by reference.

EXAMPLE 3

Treatment of *H. pylori* Infection

In this context reference is made to Walsh, J H and Peterson, W L, N. *Engl. J. Med.* 333 (1995) 984–991, which is incorporated herein by reference. This reference also provides an up-to-date guide to relevant primary literature. It should be noted that the authors only recommend without reservation eradication of *H. pylori* in patients with a definite diagnosis of duodenal or gastric ulcer. In this respect, the teaching of the present invention is different from that of Walsh and Peterson, since asymptomatic persons infected with *H. pylori* may put others, their own children or close relatives, at a mortal risk. In the context where a risk for SIDS by transmission of *H. pylori* is manifest, it is thus important to eradicate *H. pylori* in asymptomatic persons too.

It is essential that the infection be fully eradicated, preferably so ante partum. A combination treatment including a bismuth compound, such as bismuth subsalicylate or tripotassium dicitrato bismuthate, is also recommended. Antibiotics recommended for treatment of *H. pylori* infection include metronidazole, tinidazole, clarithromycin, tetracyclin, and amoxicillin. Treatment with a combination of an antibiotic or several antibiotics and a proton pump inhibitor, such as omeprazole or lansoprazole, is particularly recommended for persons with symptoms of gastric or duodenal ulcer. In milder cases of manifest gastric or duodenal ulcer, the proton pump inhibitor of said combination can be substituted by an H2-blocker, such as cimetidine, famotidine, and ranitidine. The effect of antibiotics against *H. pylori* generally increases substantially with increasing pH.

What is claimed is:

1. A method of identifying an infant's susceptibility to SIDS comprising determining an indication of *Helicobacter pylori* in a sample collected from an individual, wherein said sample is selected from the group consisting of blood, saliva, dental plaque, faeces and exhaled air, and said individual is selected from the group consisting of said infant's mother, said infant's close relative and a person expected to come into close bodily contact with said infant, and correlating the determination with susceptibility to SIDS.

2. The method of claim 1, wherein determining an indication of *Helicobacter pylori* comprises detecting antibodies to *Helicobacter pylori* in a blood sample drawn from the individual.

3. The method of claim 2, wherein the antibodies are at least one member selected from the group consisting of IgA, IgG and IgM.

4. The method of claim 1, wherein determining an indication of *Helicobacter pylori* comprises detecting carbon dioxide in the exhaled air of the individual, said carbon dioxide being formed from urea upon oral administration of a challenge dose of urea to the individual.

5. The method of claim 4, wherein the urea challenge dose comprises urea marked with $^{13}C$.

* * * * *